US009381142B2

(12) United States Patent
Preti et al.

(10) Patent No.: US 9,381,142 B2
(45) Date of Patent: *Jul. 5, 2016

(54) OLFACTORY ADAPTATION AND CROSS-ADAPTING AGENTS TO REDUCE THE PERCEPTION OF BODY ODORS

(75) Inventors: George Preti, Horsham, PA (US); Charles J. Wysocki, Collingswood, NJ (US); Leslie C. Smith, Princeton, NJ (US); Keith J. McDermott, Bound Brook, NJ (US)

(73) Assignees: Monell Chemical Senses Center, Philadelphia, PA (US); Symrise Inc., Teterboro, NJ (US)

( * ) Notice: Subject to any disclaimer, the term of this patent is extended or adjusted under 35 U.S.C. 154(b) by 37 days.

This patent is subject to a terminal disclaimer.

(21) Appl. No.: 12/816,717

(22) Filed: Jun. 16, 2010

(65) Prior Publication Data

US 2010/0254927 A1 Oct. 7, 2010

Related U.S. Application Data

(62) Division of application No. 10/342,626, filed on Jan. 15, 2003, now Pat. No. 7,763,238.

(60) Provisional application No. 60/349,111, filed on Jan. 16, 2003, provisional application No. 60/390,313, filed on Jun. 21, 2002.

(51) Int. Cl.
  *A61K 8/33* (2006.01)
  *A61K 8/34* (2006.01)
  *A61K 8/35* (2006.01)
  *A61K 8/37* (2006.01)
  *A61K 8/49* (2006.01)
  *A61Q 13/00* (2006.01)
  *A61Q 15/00* (2006.01)
  *A61Q 19/00* (2006.01)

(52) U.S. Cl.
  CPC ... *A61K 8/34* (2013.01); *A61K 8/33* (2013.01); *A61K 8/35* (2013.01); *A61K 8/37* (2013.01); *A61K 8/498* (2013.01); *A61K 8/4973* (2013.01); *A61Q 15/00* (2013.01)

(58) Field of Classification Search
  CPC ............. A61K 8/33; A61K 8/34; A61K 8/35; A61K 8/37; A61K 8/4973; A61K 8/498; A61Q 15/00; A61Q 13/00; A61Q 19/00
  USPC ............ 424/65; 512/1, 4, 5, 8, 11, 14, 19, 20, 512/21, 22, 23, 25, 26, 27
  See application file for complete search history.

(56) References Cited

U.S. PATENT DOCUMENTS

| | | | | |
|---|---|---|---|---|
| 3,923,699 A | * | 12/1975 | Komatsu et al. | 512/2 |
| 3,948,814 A | * | 4/1976 | de Rijke | 512/25 |
| 4,045,551 A | * | 8/1977 | Ueno et al. | 424/76.4 |
| 4,322,308 A | * | 3/1982 | Hooper et al. | 510/101 |
| 4,652,402 A | * | 3/1987 | Brunke et al. | 512/8 |
| 4,668,433 A | * | 5/1987 | Ochsner | 512/26 |
| 5,066,640 A | * | 11/1991 | Voss et al. | 512/21 |
| 5,135,747 A | * | 8/1992 | Faryniarz et al. | 424/401 |
| 5,501,805 A | * | 3/1996 | Behan et al. | 510/102 |
| 5,538,719 A | | 7/1996 | Preti et al. | |
| 5,552,379 A | * | 9/1996 | Winter et al. | 512/12 |
| 5,703,250 A | * | 12/1997 | Bajgrowicz | 549/369 |
| 5,711,941 A | * | 1/1998 | Behan et al. | 424/65 |
| 5,861,143 A | * | 1/1999 | Peterson et al. | 424/65 |
| 5,861,144 A | * | 1/1999 | Peterson et al. | 424/65 |
| 5,897,854 A | * | 4/1999 | Lucas et al. | 424/65 |
| 5,919,440 A | * | 7/1999 | Kaiser et al. | 424/76.4 |
| 5,972,878 A | * | 10/1999 | Sonnenberg et al. | 512/13 |
| 6,013,618 A | * | 1/2000 | Morelli et al. | 512/1 |
| 6,147,037 A | * | 11/2000 | Gardlik et al. | 510/107 |
| 6,184,419 B1 | * | 2/2001 | Berg-Schultz et al. | 568/374 |
| 6,194,375 B1 | * | 2/2001 | Ness et al. | 512/4 |
| 6,252,120 B1 | * | 6/2001 | Dilk et al. | 568/393 |
| 6,420,334 B1 | * | 7/2002 | Surburg et al. | 512/25 |
| 6,869,923 B1 | * | 3/2005 | Cunningham et al. | 512/4 |
| 2002/0049257 A1 | * | 4/2002 | Natsch | 514/715 |
| 2003/0083225 A1 | * | 5/2003 | Kappey et al. | 512/14 |

(Continued)

FOREIGN PATENT DOCUMENTS

| | | |
|---|---|---|
| EP | 0955035 A1 | 11/1999 |
| EP | 0 761 664 B1 * | 3/2001 |
| EP | 1 169 999 A2 * | 1/2002 |
| GB | 1311060 A | 3/1973 |
| WO | WO-9856429 A1 | 12/1998 |
| WO | WO-9944575 A1 | 9/1999 |

OTHER PUBLICATIONS

J. Handley and D. Burrows, "Allergic contact dermatitis from the synthetic fragrances Lyral and acetyl cedrene in separate underarm deodorant preparations", Contact Dermatitis, 1994, 31, 288-290.*

(Continued)

*Primary Examiner* — John Pak
*Assistant Examiner* — Nathan W Schlientz
(74) *Attorney, Agent, or Firm* — Dilworth & Barrese LLP

(57) ABSTRACT

Deodorant compositions are disclosed comprising a cross-adapting agent, alone or in combination with other such agents, in an amount effective to reduce perception of malodor. Deodorant compositions are also disclosed comprising a cross-adapting agent, alone or in combination with other such agents, in an amount effective to reduce perception of gender-specific malodor. The methods feature reducing perceived body odor comprising administering a deodorant composition wherein the composition comprises an amount of cross-adapting agent effective to reduce perception of such odor. Other methods feature blocking perceived body odor comprising administering a deodorant composition wherein the composition comprises an amount of cross-adapting agent effective to occupy an odorant receptor site, thereby blocking interaction of the site with other odorants. Methods of making deodorant compositions are also provided wherein a cross-adapting agent, alone or in combination with other such agents, are included in an amount effective to reduce perception of malodor.

2 Claims, No Drawings

(56) References Cited

U.S. PATENT DOCUMENTS

2003/0087774 A1* 5/2003 Smith et al. ............... 510/101
2003/0087776 A1* 5/2003 Heltovics et al. .......... 510/101

OTHER PUBLICATIONS

S.A. Hendriks, M.T. Bousema and C.J.W. van Ginkel, "Allergic contact dermatitis from the fragrance ingredient Lyral in underarm deodorant", Contact Dermatitis, 1999, 41, 119.*

K. Bauer, D. Garbe and H. Surburg, "Common Fragrance and Flavor Materials: Preparation and Uses", Wiley-VCH Verlag GmbH, $4^{th}$ Ed., 2001, p. 41, 42, 59, 61, 62, 70, 71, 83, 89, 101, 102 and 150.*

Database WPI Week 200169 Thomson Scientific, London, GB; AN 2001-605220 XP002454986 & JP 2001 181164 A (Lion Corp) Jul. 3, 2001.

Examination Report, EP Application No. 03 710 691.1, dated Jul. 14, 2010.

* cited by examiner

OLFACTORY ADAPTATION AND CROSS-ADAPTING AGENTS TO REDUCE THE PERCEPTION OF BODY ODORS

CROSS-REFERENCE TO RELATED APPLICATIONS

This claims the benefit of priority under 35 U.S.C. §119(e) from provisional U.S. Application Ser. Nos. 60/349,111, filed on Jan. 16, 2002, and 60/390,313, filed Jun. 21, 2002, and is a continuation of application Ser. No. 10/342,626, filed on Jan. 15, 2002, all of which are incorporated herein by reference in their entirety.

FIELD OF THE INVENTION

The present invention relates to human olfactory adaptation, including human olfactory cross-adaptation, and to methods, cross-adapting agents and compositions to reduce the perception of body odors, including gender-specific body odors.

BACKGROUND OF THE INVENTION

Olfactory adaptation is a phenomenon that is generally understood to include a decrease in sensitivity to an odorant that results from exposure to that odorant. Such adaptation can result, at least in part, from peripheral events, such as fatigue of the receptor.

Cross-adaptation is a phenomenon that is generally understood to include a decrease in sensitivity to one odorant, e.g., odorant B, that results from exposure to a different odorant, e.g., odorant A. Cross-adaptation can result from competition for receptor sites in the periphery. For example, when odorant A occupies the receptors that would be preferentially occupied by odorant B, it may induce cross-adaptation in that receptor and desensitize the population of receptors to odorant B.

Alternatively, cross-adaptation can result from the processing of information about odors within brain circuitry. For example, if odorants A and B both utilize, at least in part, the same circuits, and the system is occupied by processing information about odorant A, then the individual will be less sensitive to odorant B because there is competing information being processed. If odorant B is an unpleasant or unwanted odor, for example, that of underarm sweat, also called axillary odor, and odorant A is a pleasant-smelling odorant or fragrance, then the presence of the pleasant-smelling odorant could act as a cross-adapting agent to diminish the impact of the axillary odor.

Body odors, including axillary odors, are produced by males and females. It is generally recognized that both sexes produce more axillary odors during times of stress and/or strong emotional situations. The apocrine glands are sensitive to blood levels of epinephrine (adrenaline). Stress and other strong emotional situations increase blood levels of adrenaline causing the apocrine glands to rapidly secrete relatively large amounts of their contents to the skin surface. Stress-derived axillary odor is produced during episodes of high apocrine gland output via rapid metabolism of apocrine gland-rich axillary secretions by cutaneous axillary bacteria.

Although it is often desirable to reduce the perception of malodors by both sexes, females are known to be more sensitive to a number of odorants including, but not limited to, axillary odorants and display, on average, greater olfactory sensitivity to odorants than males. In addition, females exhibit greater olfactory sensitivity to odorants at certain times in their menstrual cycle. It is desirable to identify methods and agents for reducing the perception of male and female body odors by women, as well as the perception of male and female body odors by men.

Agents that are capable of reducing the perception of body odors may be used in cosmetic and personal products, including, but not limited to, gender-specific cosmetics and personal products. They may also be used in compositions that reduce the perception of malodors, including gender-specific malodors. For example, it could be desirable to include cross-adapting agents in goods directed to females that selectively block or reduce male or female malodors. Similarly, it could be desirable to include fragrances in goods directed to males that selectively block or reduce male or female malodors. It could also be desirable to use such agents in compositions and methods that are not gender-specific.

SUMMARY OF THE INVENTION

The present invention provides deodorant compositions comprising at least one cross-adapting agent alone or in combination with other such agents, in an amount effective to reduce perception of male and female malodor. The present invention also provides gender-specific deodorant compositions comprising at least one cross-adapting agent alone or in combination with other such agents, in an amount effective to reduce perception of male malodor. The present invention further provides other gender-specific deodorant compositions comprising at least one cross-adapting agent alone or in combination with other such agents, in an amount effective to reduce perception of female malodor. Such malodors may include, but are not limited to, axillary odors, whether or not such axillary odors are stress-derived.

In one preferred embodiment, the cross-adapting agent or combination of such agents comprises from about 0.1% to about 10% by weight of the deodorant composition.

The present invention also provides methods of reducing perception of body odor or malodor comprising administering a deodorant composition that includes a cross-adapting agent alone or in combination with other such agents in an amount effective to reduce perception of male and female body odor. The present invention also provides methods of reducing perceived male body odor or malodor, as well as methods of reducing perceived female body odor comprising administering a deodorant composition comprising an amount of cross-adapting agent effective to reduce perception of a gender specific body odor.

Further, the present invention provides methods of blocking male or female body odor by administering deodorant compositions comprising an amount of cross-adapting agent or combination of such agents effective to occupy an odorant receptor site thereby blocking interaction of the site with other odorants.

In a further embodiment of the present invention, methods are provided for making a deodorant composition comprising providing a cross-adapting agent alone or in combination with other such agents in an amount effective to reduce perception of malodor.

DETAILED DESCRIPTION

Cross-adaptation has been found to be an effective methodology for inhibiting the perception of body malodors. It has been found that significant cross-adaptation may occur between certain adapting agents and malodors, including gender-specific malodors. For example, it has been found that certain adapting agents reduce the perceived intensity by females of the body odor from males. Also, it has been found that certain adapting agents reduce the perceived intensity by males of the body odor from males. In addition, it has been found that certain adapting agents reduce the perceived intensity by males of the body odor from females. Finally, it has been found that certain adapting agents reduce the perceived intensity by females of the body odor from females. For the malodors from each gender, these include axillary odors.

The terms "a, an, and the" are used herein include the plurals of those same words.

The term "malodor" as used herein refers to an odorant that may be perceived by some to be unpleasant, including but not limited to body odor, odors originating from bathrooms, clothes hampers, locker rooms, gymnasiums, and the like.

The term "body odor" as used herein refers to a malodor associated with and/or that emanates from the human body including, but not limited to, axillary odor, fecal/urine odors, and odors related to the female menstrual cycle.

The term "axillary odor" as used herein refers to a malodor from human armpits including, but not limited to, apocrine secretions and/or odors generated from stress.

The term "stress-derived axillary odor" as used herein refers to axillary odor resulting from bacterial metabolism or base hydrolysis of apocrine gland secretions.

The term "cross-adapting agent" as used herein refers, without limitation, to any adapting agent, odorant, compound, agent, fragrance, or combination thereof that is effective in reducing or blocking the perception of a malodor after exposure to the cross-adapting agent.

The term "reducing" as used herein refers to a decrease in sensitivity to an odorant, or its perceived intensity, through the process of adaptation or cross-adaptation.

The term "blocking" as used herein refers to the ability of a cross-adapting agent to occupy an odorant receptor site and block interaction of the site with other odorants.

The term "deodorant composition" as used herein refers to an item or product or cosmetic that may be used to reduce the perceived intensity or block malodor. The deodorant composition may be used for a locality such as human axillae, a bathroom, a clothes hamper, a locker room, a gymnasium, or on a surface. Such deodorants may be distributed or dispersed in, on, or around the area of the locality by methods known to those in the art, such as by spraying or by evaporation of a liquid or solid containing at least one cross-adapting agent. Suitable carriers are known to those skilled in the art and vary depending upon the method of distribution or dispersement of the deodorant.

In general, the proposed compositions and methods use and/or incorporate into products cross-adapting agents (alone or in combination) to block and/or reduce the perception of malodors, including body odors, such as axillary odors, fecal/urine odors, and odors related to the female menstrual cycle. Useful cross-adapting agents include agrumex (2-tert-butyl cyclohexyl acetate; 2-(1,1-dimethylethyl)-cyclohexanyl acetate); C14 aldehyde (1,4 undecanolide; gamma-undecalactone); ambrettolide (cyclohexadec-6-olide; oxacycloheptadec-10-en-2-one; omega-6-hexadecenlactone; 6-hexadecanolide); anisic aldehyde (4-methoxybenzaldehyde); calone 1951 (7-methyl-314-dihydro-2H-1,5-benzodioxepin-3-one); l-carvone (1-1menthyl-4-iso-propenyl-6-cyclohexen-2-one; carvol), CEDRAIVIBER® (cedryl methyl ether); citronellol 950 (3,7-dimethyl-6-octen-1-ol); citrylal (Octa-2,6-dien; 1,1-dimethoxy-3-7-dimethyl) as supplied by Haarmann & Reimer, Product No. 690980; CLARITONE® (2,4,4,7-tetramethyl-oct-6-en-3-one), cpd supra (15-pentadecalactone; cyclopentadecanolide supra; oxacyclohexadecan-2-one); α-damascone (1-(2,6,6-trimethyl-2-cyclohexen-1-yl)-2-buten-1-one); Δ-damascone (1-(2,6,6-trimethyl-3-cyclohexen-1-yl)-2-buten-1-one); datilat (Cyclohexyl methyl carbinol crotonate) dihydromyrcenol (3-methylenE-7-methyloctanol-7; 2,6-dimethyl-7-octen-2-ol); dynascone 10 (1-(5,5-dimethyl-1-cyclohexen-1-yl)4-penten-1-one); ethyl vanillin (3-Ethoxy-4-hydroxybenzaldehyde); eugenol (2-methoxy-1-hydroxy-4-allylbenzene); evernyl (methyl 2,4-dihydroxy-3,6-dimethylbenzoate; 4-allyl-2-methoxyphenol; 4-allylguaiacol); FARENAL® (2,6,10-trimethyl-9-undecenal); floropal (2,4,6-trimethyl-4-phenyl-1,3-dioxane); GLOBALIDE® (oxacyclohexadecen-2-one); GLOBANONE® (cyclohexadecen-5-one-1; cyclohexadecenone); HEDIONE® (methyl dihydro jasmonate); cis-3-hexenol (cis-3-hexenol-1-ol); hexyl salicylate (hexyl-2-hydroxybenzoate); hexylcinnamic aldehyde (alpha-hexylcinnamaldehyde); α-ionone (4-(2,2,6-trimethyl-2cyclohexen-1-yl)-3-buten-2-one); β-ionone (4-(2,6,6-trimethyl-2cyclohexen-1-yl)-3-buten-2-one); ISO E SUPER® (octahydro-2,3,8,8-tetramethyl-2-acetonaphthone; and 2-acetyl-1,2,3,4,6,7,8-octahydro-2,3,8,8-tetramethyl naphalene); isoananat (allyl cyclohexyloxyacetate); isoraldeine 70 (alpha-n-methylionone; cyclocitrylidene methyl ethyl ketone); lilial (p-tert-butyl-alpha-methyldihydrocinnamaic aldehyde; 4-(1,1-dimethylethyl)-alpha-methylbenzenepropanal; p-t-bucinal), lyral (4-(4-hydroxy-4-methylpentyl)-3-cyclohexenE-1-carboxaldehyde)); MAJANTOL® (2,2-dimethyl-3-(methylphenyl) propanol); menthyl acetate rf (4-menthyl-3-yl acetate); mugetanol (1-(4-isopropylcyclohexyl)ethanol); nerolione (1-(3-bethyl-2-benzofuranyl)-ethanone); E-, Z-isomers (3:1) of 3-methyl-2-octenoic acid ethyl esters; H&R odor neutralizer (supplied by Haarmann and Reimer, Product No. D61012); oryclone special (4-tertbutylcyclohexyl acetate; 4-(1,1-dimethylethyl) cyclohexyl acetate); patchouli oil; phenylethyl alcohol; E-isomer of 3-methyl-2-pentenoic acid ethyl ester; E-isomer of 3-methyl-2-octenoic acid ethyl ester; Z-isomer of 3-methyl-2-pentenoic acid ethyl ester; Rosaphen® (2-methyl-5-phenylpentan-1-ol); rose oxide hc (4-methyl-2-(2-methyl-1-propenyl)tetrahydro-2H-pyran) Isobornyl Cyclohexanol (isobornyl cyclohexanol); Sandranol® (2-ethyl-4-(2,2,3-trimethyl-3-cyclopenten-1-yl)-2-buten-1-ol); tetrahydro linalool (3,7-Dimethyloctan-3-ol); timbranol (Isomethyltetrahydroionol); tonalide (7-Acetyl-1,1,3,4,4,6-hexamethyltetralin); and vertocitral (2,4-dimethyl-3-cyclohexene-1-carboxaldehyde).

In selecting an agent or agents for use in the described methods and compositions, a magnitude of reduction in the intensity of odor is a relevant consideration. For example, agents that produce a high reduction in the intensity of a malodor can be described as "best," agents that show a moderate reduction can be labeled as "good," and agents that have the least effect on reducing the magnitude of malodor intensity can be described as "poor." "Best", "good", and "poor" describe the magnitude of cross-adaptation that an agent exhibits against a malodor and do not necessarily rely upon the results of statistical evaluations. A product can be constructed in a way to include as many "best" or "good" materials as desirable, but the use of "poor" materials is not precluded. The use of poor agents may be desirable based on, for example, economics or hedonics, and "poor" agents may, in some instances, be combined with "good" or "best" agents in order to achieve a desired reduction or blockage of malodor. By using at least one or a combination of "best" and "good" materials in a product, the effectiveness in reducing and/or blocking malodors, including stress-derived axillary odor, may be increased.

The present invention provides deodorant compositions comprising at least one cross-adapting agent alone or in combination with other such agents, in an amount effective to reduce perception of male and female malodor. The present invention also provides gender-specific deodorant compositions comprising at least one cross-adapting agent alone or in combination with other such agents, in an amount effective to reduce perception of male malodor. The present invention further provides other gender-specific deodorant compositions comprising at least one cross-adapting agent alone or in combination with other such agents, in an amount effective to reduce perception of female malodor. Such malodors may include, but are not limited to, axiallary odors, whether or not such axillary odors are stress-derived.

In one preferred embodiment, the cross-adapting agent or combination of such agents comprises from about 0.1% to about 10% by weight of the deodorant composition.

Cross-adapting agents that have been identified by a group of subjects tested to be "best" or "good" for reducing and/or blocking either male or female malodors include agrumex, C14 aldehyde, ambrettolide, anisic aldehyde, calone 1951, l-carvone, CEDRAMBER®, citronellol 950, citrylal, CLARITONE®, cpd supra, α-damascone, Δ-damascone, dihydromyrcenol, dynascone 10, ethyl vanillin, eugenol, evernyl, FARENAL®, floropal, GLOBALIDE®, GLOBANONE®, cis-3-hexenol, hexyl salicylate, hexylcinnamic aldehyde, α-ionone, β-ionone, isoananat, isoraldeine 70, lilial, lyral, MAJANTOL®, menthyl acetate rf, mugetanol, nerolione, E-, Z-isomers (3:1) of 3-methyl-2-octenoic acid ethyl esters, H&R odor neutralizer (D61012), oryclone special, patchouli oil, phenylethyl alcohol, E-isomer of 3-methyl-2-pentenoic acid ethyl ester, E-isomer of 3-methyl-2-octenoic acid ethyl ester, Z-isomer of 3-methyl-2-pentenoic acid ethyl ester, Rosaphen®, rose oxide hc, Isobornyl Cyclohexanol, Sandranol®, tetrahydro linalool, tonalide, and vertocitral.

In a preferred embodiment, the compositions and methods for reducing perception of malodor utilize one or more cross-adapting agents selected from a group that includes ambrettolide, calone 1951, citrylal, cpd supra, dihydromyrcenol, GLOBALIDE®, GLOBANONE®, lilial, lyral, E-, Z-isomers (3:1) of 3-methyl-2-octenoic acid ethyl esters, H&R odor neutralizer (D61012), E-isomer of 3-methyl-2-pentenoic acid ethyl ester, E-isomer of 3-methyl-2-octenoic acid ethyl ester, Z-isomer of 3-methyl-2-pentenoic acid ethyl ester, and vertocitral.

Cross-adapting agents that have been identified by a group of men perceiving male malodor to be "best" include l-carvone, citrylal, CLARITONE®, Δ-damascone, dihydromyrcenol, dynascone 10, eugenol, isoananat, menthyl acetate rf, E-, Z-isomers (3:1) of 3-methyl-2-octenoic acid ethyl esters, H&R odor neutralizer (D61012), Z-isomer 3-methyl-2-pentenoic acid ethyl ester, Rosaphen®, and tertahydro linalool. Cross-adapting agents that were rated by this group as "good" include agrumex, C14 aldehyde, CEDRAMBER®, citronellol 950, floropal, GLOBALIDE®, cis-3-hexenol, hexylcinnamic aldehyde, mugetanol, nerolione, oryclone special, phenylethyl alcohol, E-isomer 3-methyl-2-pentenoic acid ethyl ester, Isobornyl Cyclohexanol, Sandranol®, tonalide, and vertocitral. These may be utilized, alone or in combination with other cross-adapting agent(s), in preferred embodiments directed to reducing the perception of male malodor by men.

In a preferred embodiment, a deodorant composition is provided that includes agrumex, C14 aldehyde, CEDRAMBER®, CLARITONE®, eugenol, Δ-damascone, dihydromyrcenol, dynascone 10, GLOBALIDE®, cis-3-hexenol, hexylcinnamic aldehyde, isoananat, menthyl acetate rf, oryclone special, phenylethyl alcohol, Rosaphen®, Sandranol®, tetrahydro linalool, or vertocitral, alone or in combination with other cross-adapting agent(s).

Cross-adapting agents that have been identified by a group of women perceiving male malodor to be "best" include l-carvone, CLARITONE®, E-, Z-isomers (3:1) of 3-methyl-2-octenoic acid ethyl esters, H&R odor neutralizer (D61012), and vertocitral. Cross-adapting agents that were rated by this group as "good" include citronellol 950, citrylal, Δ-damascone, dihydromyrcenol, cis-3-hexenol, hexylcinnamic aldehyde, phenylethyl alcohol, E-isomer 3-methyl-2-pentenoic acid ethyl ester, and rose oxide hc. These may be utilized, alone or in combination with other cross-adapting agent(s), in preferred embodiments directed to reducing the perception of male malodor by women.

Cross-adapting agents that have been identified by a group of men perceiving female malodor to be "best" include anisic aldehyde, CLARITONE®, dihydromyrcenol, ethyl vanillin, floropal, cis-3-hexenol, isoraldeine 70, E-, Z-isomers (3:1) of 3-methyl-2-octenoic acid ethyl esters, oryclone special, patchouli oil, and vertocitral. Cross-adapting agents that were rated by this group as "good" include C14 aldehyde, calone 1951, l-carvone, CEDRAIVIBER®, citronellol 950, cpd supra, dynascone 10, eugenol, FARENAL®, GLOBANONE®, hexylcinnamic aldehyde, α-ionone, β-ionone, isoananat, lilial, lyral, MAJANTOL®, menthyl acetate rf, phenylethyl alcohol, E-isomer of 3-methyl-2-octenoic acid ethyl ester, Rosaphen®, rose oxide hc, and Sandranol®. These may be utilized, alone or in combination with other cross-adapting agent(s), in preferred embodiments directed to reducing the perception of female malodor by men.

Cross-adapting agents that have been identified by a group of women perceiving female malodor to be "best" include agrumex, l-carvone, floropal, E-, Z-isomers (3:1) of 3-methyl-2-octenoic acid ethyl esters, patchouli oil, and vertocitral. Cross-adapting agents that were rated by this group as "good" include C14 aldehyde, ambrettolide, anisic aldehyde, calone 1951, CEDRAIVIBER®, citronellol 950, CLARITONE®, cpd supra, α-damascone, dihydromyrcenol, dynascone 10, eugenol, evernyl, GLOBALIDE®, cis-3-hexenol, hexyl salicylate, α-ionone, menthyl acetate rf, H&R odor neutralizer (D61012), rose oxide hc, and Sandranol®. These may be utilized, alone or in combination with other cross-adapting agent(s), in preferred embodiments directed to reducing the perception of female malodor in women.

In a preferred embodiment, a deodorant composition is provided that includes agrumex, C14 aldehyde, ambrettolide, anisic aldehyde, CLARITONE®, dihydromyrcenol, dynascone 10, evernyl, GLOBALIDE®, hexyl salicylate, α-ionone, cpd supra, menthyl acetate rf, patchouli oil, Sandranol®, or vertocitral, alone or in combination with other cross-adapting agent(s).

The present invention also provides methods of reducing perception of body odor or malodor comprising administering a deodorant composition comprising a cross-adapting agent alone or in combination with other such agent(s) in an amount effective to reduce perception of body odor. For example, the present invention provides methods of reducing perceived male body odor or malodor comprising administering a deodorant composition comprising an amount of cross-adapting agent effective to reduce perception of male body odor. In one embodiment, a deodorant composition using, for example, "best" and "good" agents comprising an agent selected from a group that includes: agrumex, C14 aldehyde, l-carvone, CEDRAMBER®, citronellol 950, citrylal, CLARITONE®, Δ-damascone, dihydromyrcenol, dynascone 10, eugenol, floropal, GLOBALIDE®, cis-3-hexenol, hexylcinnamic aldehyde, isoananat, menthyl acetate rf, mugetanol, nerolione, E-, Z-isomers (3:1) of 3-methyl-2-octenoic acid ethyl esters, H&R odor neutralizer (D61012), oryclone special, phenylethyl alcohol, E-isomer of 3-methyl-2-pentenoic acid ethyl ester, Z-isomer of 3-methyl-2-pentenoic acid ethyl ester, Rosaphen®, rose oxide hc, Isobornyl Cyclohexanol, Sandranol®, tetrahydro linalool, tonalide, vertocitral, and combinations thereof is provided.

Other methods are provided in the present invention of reducing perceived female body odor comprising administering a deodorant composition comprising an amount of cross-adapting agent effective to reduce perception of female body odor. In one embodiment using, for example, "best" and "good" agents, a deodorant composition comprising an agent selected from a group that includes: agrumex, C14 aldehyde, ambrettolide, anisic aldehyde, calone 1951, l-carvone, CEDRAIVIBER® citronellol 950, CLARITONE®, cpd supra, α-damascone, dihydromyrcenol, dynascone 10, ethyl vanillin, eugenol, evernyl, FARENAL®, floropal, GLOBALIDE®, GLOBANONE®, cis-3-hexenol, hexyl salicylate, hexylcinnamic aldehyde, α-ionone, β-ionone, isoananat, isoraldeine 70, lilial, lyral, MAJANTOL®, menthyl acetate rf, E-, Z-isomers (3:1) of 3-methyl-2-octenoic acid ethyl esters, H&R odor neutralizer (D61012), oryclone special, patchouli oil, phenylethyl alcohol, E-isomer of 3-methyl-2-octenoic acid ethyl ester, Rosaphen®, rose oxide hc, Sandranol®, vertocitral, and combinations thereof is provided.

Further, the present invention provides methods of blocking male or female body odor by administering deodorant compositions comprising an amount of cross-adapting agent(s) effective to occupy an odorant receptor site thereby blocking interaction of the site with other odorants. In one method, directed to blocking male malodor using "best" and "good" adapting agents, for example, a deodorant composition comprising an agent selected from a group that includes: agrumex, C14 aldehyde, l-carvone, CEDRAMBER®, citronellol 950, citrylal, CLARITONE®, Δ-damascone, dihydromyrcenol, dynascone 10, eugenol, floropal, GLOBALIDE®, cis-3-hexenol, hexylcinnamic aldehyde, isoananat, menthyl acetate rf, mugetanol, nerolione, E-, Z-isomers (3:1) of 3-methyl-2-octenoic acid ethyl esters, H&R odor neutralizer (D61012), oryclone special, phenylethyl alcohol, E-isomer of 3-methyl-2-pentenoic acid ethyl ester, Z-isomer of 3-methyl-2-pentenoic acid ethyl ester, Rosaphen®, rose oxide hc, Isobornyl Cyclohexanol, Sandranol®, tonalide, vertocitral, alone or in combination with other cross-adapting agent(s) is provided. In another method, directed to blocking female malodor using "best" and "good" adapting agents, for example, a deodorant composition comprising an agent selected from a group that includes: agrumex, C14 aldehyde, ambrettolide, anisic aldehyde, calone 1951, l-carvone, CEDRAMBER®, citronellol 950, CLARITONE®, cpd supra, α-damascone, dihydromyrcenol, dynascone 10, ethyl vanillin, eugenol, evernyl, FARENAL®, floropal, GLOBALIDE®, GLOBANONE®, cis-3-hexenol, hexyl salicylate, hexylcinnamic aldehyde, α-ionone, β-ionone, isoananat, isoraldeine 70, lilial, lyral, MAJANTOL®, menthyl acetate rf, E-, Z-isomers (3:1) of 3-methyl-2-octenoic acid ethyl esters, H&R odor neutralizer (D61012), oryclone special, patchouli oil, phenylethyl alcohol, E-isomer of 3-methyl-2-octenoic acid ethyl ester, Rosaphen®, rose oxide hc, Sandranol®, vertocitral, alone or in combination with other cross-adapting agent(s) is provided.

In a further embodiment of the present invention, methods of making a deodorant composition comprising providing a cross-adapting agent alone or in combination with other such agents in an amount effective to reduce perception of malodor is provided. Cross-adapting agents can be present in a deodorant composition from about 0.1% to about 10% by weight of the deodorant composition, in certain preferred embodiments.

Methods

In a series of studies, some involving malodors and others using pleasant-smelling odorants, we demonstrated the feasibility of a protocol we developed for exploring adaptation and cross-adaptation in human olfaction (J. D. Pierce, Jr., C. J. Wysocki, and E. V. Aronov, *Mutual cross-adaptation of the volatile steroid androstenone and a non-steroid functional analog*, 18 Chemical Senses 245-256 (1993); J. D. Pierce, Jr., X-N. Zeng, E. V. Aronov, G. Preti, and C. J. Wysocki, *Cross-adaptation of sweaty-smelling 3-methyl-2-hexenoic acid by a structurally-similar, pleasant-smelling odorant*, 20 Chemical Senses 401-411 (1995); J. D. Pierce, Jr., C. J. Wysocki, E. V. Aronov, J. B. Webb, and R. M. Boden, *The role of perceptual and structural similarity in cross-adaptation,* 21 Chemical Senses 223-237 (1996); J. D. Pierce, Jr., D. H. Blank, E. V. Aronov, Z. Guo, G. Preti, and C. J. Wysocki, *Cross-adaptation of sweaty-smelling 3-methyl-2-hexenoic acid by its ethyl esters is determined by structural similarity,* 47 Journal of the Society of Cosmetic Chemists 363-375 (1996); J. D. Pierce, Jr., D. H. Blank, G. Preti, and C. J. Wysocki, *Reduction in the sweaty smell of 3-methyl-2-hexenoic acid by cross-adaptation using its pleasant-smelling methyl esters.* 49 Journal of Cosmetic Science 369-376 (1998); each incorporated herein by reference in their entirety).

The procedure relies upon an individual constantly sniffing an adapting agent, such as a fragrance, and occasionally a test odorant. Perceived intensity of the test odorant is obtained by using psychophysical, magnitude-estimation procedures. These perceived intensities are obtained every 30 seconds over the test period, and are then compared with baseline perceived intensities obtained before the individual began sniffing the adapting agent. Throughout the testing we observe adaptation to the adapting agent. Results during trials with an inserted test odorant, such as the axillary odor used here, are believed to be reasonably predictive. If the perceived intensity of the test odorant decreases during the test, then the adapting agent cross-adapts the test odorant and becomes a cross-adapting agent. If the cross-adapting agent is itself not offensive, then the cross-adapting agent becomes a candidate for use in formulations in consumer products to ameliorate malodors, such as axillary odor or fecal/urine odors, and odors related to the female menstrual cycle.

Using these techniques, we previously demonstrated that a homologous series of 3-methyl-α,β-unsaturated acid ethyl esters, e.g., 3-methyl-2-hexenoic acid ethyl esters, 3-methyl-2-octenoic acid ethyl esters, and 3-methyl-2-pentenoic acid ethyl esters, could be used to ameliorate unpleasant body odors (J. D. Pierce, Jr., X-N. Zeng, E. V. Aronov, G. Preti, and C. J. Wysocki, *Cross-adaptation of sweaty-smelling 3-methyl-2-hexenoic acid by a structurally-similar, pleasant-smelling odorant,* 20 Chemical Senses 401-411 (1995); U.S. Pat. No. 5,538,719 (Issued Jul. 23, 1996); J. D. Pierce, Jr., D. H. Blank, E. V. Aronov, Z. Guo, G. Preti, and C. J. Wysocki, *Cross-adaptation of sweaty-smelling 3-methyl-2-hexenoic acid by its ethyl esters is determined by structural similarity,* 47 Journal of the Society of Cosmetic. Chemists 363-375 (1996); J. D. Pierce, Jr., D. H. Blank, G. Preti, and C. J. Wysocki, *Reduction in the sweaty smell of 3-methyl-2-hexenoic acid by cross-adaptation using its pleasant-smelling methyl esters.* 49 Journal of Cosmetic Science 369-376 (1998); C. J. Wysocki, L. Connolly, J. Louie, G. Preti, and M. Gill, *Cross-adaptation of mercaptoethanol by the ethylesters* of *3-methyl-2-pentenoic acid,* 23 Chem. Senses. 598 (1999); each incorporated herein by reference in their entirety).

Applying the foregoing methods, we have now identified further compounds, such as fragrances, and combinations of compounds capable of doing so, and further identified gender-specificity for some of these compounds.

Collection of secretions: Apocrine secretions obtained under stressed conditions provided the axillary odor that was used as the test odorant to evaluate the effectiveness of various adapting agents. Secretions were obtained from males (ages 20 to 60 years) and females (ages 20 to 40 years) in good health. The donors had a history of axillary odor production and consistent use of underarm products to control odor. Volunteers prepared their axillae for collection of apocrine secretions by refraining from deodorant use for 3 days and shaving their axillae the morning of the collection day.

Volunteers were rested in a supine position. The axillary regions were washed with isopropanol-soaked pads and injected intradermally with 1:10,000 adrenalin (in physiologic saline). This injection stimulated the secretion of apocrine gland secretions, which were collected in 10 µl pipettes, passed into 0.25 ml Eppendorf tubes, and stored on ice (or frozen for longer storage). The amount of secretion collected varied greatly with the individual subject (≤10 µl). The apocrine secretions from each volunteer were combined by consecutively washing each Eppendorf tube with 2×300 µl of doubly distilled water. This aqueous-apocrine fluid was transferred to a 5 ml round-bottomed flask for hydrolysis. X-N. Zeng, J. J. Leyden, J. G. Brand, A. I. Spielman, K. J. McGinley, G. Preti, *An Investigation of Human Apocrine Gland Secretion for Axillary Odor Precursors,* 18 J. Chem. Ecol. 1039-1055 (1992); X-N. Zeng, J. J. Leyden, A. I. Spielman and G. Preti Analysis *of the characteristic human female axillary odors: Qualitative comparison to males.* 22 J. Chem. Ecol. 237-257 (1996).

Production of odor: To produce quantities of stress-derived axillary odor for testing purposes, we hydrolyzed the apocrine secretion. The aqueous solution was refluxed for 20 min with 0.5 ml, 5% aqueous sodium hydroxide under a stream of nitrogen. The mixture was allowed to cool to room temperature, and then it was cooled in ice prior to being acidified with 6 N HCl to pH 2. The resulting axillary odor developed in the reaction mixture upon acidification was used as the test odorant. The axillary odors generated by this in vitro technique are analogous to the malodors produced by stressed individuals.

Example 1

Cross-Adaptation of Male Stress-Derived Axillary Odor

Sixteen (16) individuals (8 of each gender) served on an odor panel. Subjects ranged in age from 22 to 55 years (mean 32.7±10.6 s.d.), were not pregnant (by verbal report), and were all non-smokers. All panel members were screened for adequate use of magnitude estimation (some people have difficulties maintaining a ratio scale, i.e., when an odorant is half as strong as the previous, these people fail to provide a number that is half the previous estimate) and further trained in its use during 2-3 training sessions. All 16 subjects were tested with samples of male malodor compared to each of the potential cross-adapting agents.

Male stress-derived axillary odor, produced as described above, was presented in glass vials for the subjects to sniff once to obtain the first baseline of perceived intensity using magnitude estimation. Subsequently, subjects continuously sniffed from an adapting jar that contained only diluent, which was odorless, light, white, mineral oil. After 30 seconds, another baseline perceived intensity for axillary odor was obtained with a single sniff of the axillary odor. Again, the sniff of axillary odor was followed by continued sniffs from an adapting jar that contained only diluent. After another 30 seconds, a third baseline estimate was obtained in a similar manner.

In a single test, the diluent was then replaced with one and only one adapting agent, and for each sniff from the adapting jar thereafter, subjects sniffed the adapting agent. On the first sniff, the perceived intensity of the adapting agent was obtained. Subjects then continued to sniff from the adapting jar. Every 30 seconds during the next 3 minutes, subjects sniffed and rated the perceived intensity of the axillary odor from the glass vial. This process was repeated for each adapting agent.

At the conclusion of the 4-minute test, we had obtained 3 baseline measures of perceived intensities of axillary odor and 6 perceived intensities of axillary odor during adaptation and, in some cases, cross-adaptation. In addition, we obtained 3 perceived intensities of the adapting agent and 3 perceived intensities of the diluent.

Each test session contained 5 or 6 tests during which panelists provided perceived intensities during exposures to 5 or 6 adapting agents. Between adapting agents, each panelist was given a 5-minute rest. Across panelists, the order of the 5 or 6 adaptation tests was randomized. This was done because some of the adapting agents could have cross-adapted among themselves.

Several adapting agents were tested in the procedure to determine which could reduce the perception of the male stress-derived axillary odor produced in vitro. Subjects were asked to provide perceived odor intensities, or magnitude estimations, before and during exposure to each of several odorants. The adapting agents were chosen from among the following: agrumex, C14 aldehyde, ambrettolide, l-carvone, CEDRAMBER®, citronellol 950, citrylal, CLARITONE®, cpd supra, α-damascone, Δ-damascone, datilat, dihydromyrcenol, dynascone 10, eugenol, FARENAL®, floropal, GLOBALIDE®, HEDIONE®, Z-isomer 3-methyl-2-pentenoic acid ethyl ester, cis-3-hexenol, hexyl salicylate, hexylcinnamic aldehyde, ISO E SUPER®, isoananat, menthyl acetate rf, mugetanol, nerolione, E-, Z-isomers (3:1) of 3-methyl-2-octenoic acid ethyl esters, H&R odor neutralizer (D61012) (a product supplied by Haarmann & Reimer), oryclone special, phenylethyl alcohol, E-isomer 3-methyl-2-pentenoic acid ethyl ester, Rosaphen®, rose oxide hc, Isobornyl Cyclohexanol, Sandranol®, tertahydro linalool, timbranol, tonalide, and vertocitral.

Magnitude estimations provided by each test subject were normalized compared to each subject's rating of a targeted malodor, e.g. male stress-derived axillary odor. A subject's rating of the intensity of a targeted malodor was standardized to a scale of 100, and then subsequent ratings after exposure to cross-adapting agents were standardized accordingly. Such standardized data was then analyzed for statistical significance and is reflected in Table 1. Male and female panel members did not differ in their perceived intensities of the adapting agents or their perceived intensities of the stress-derived axillary odor.

Although in this case "p values" were used to identify adaptive agents, other methods for assessing differences in perceived intensity of odors could also be used. When the results of the panel as a whole were considered, twelve (12) cross-adapting agents were identified among the adapting agents, where adequate cross-adaptation at a level of <0.05 was produced. These cross-adapting agents included C14 aldehyde, l-carvone, citronellol 950, citrylal, dynascone 10, eugenol, floropal, oryclone special, E-isomer 3-methyl-2-pentenoic acid ethyl ester; rose oxide hc, Sandranol®, and vertocitral. Certain of the cross-adapting agents were superior, producing significant cross-adaptation of p<0.01. These included hexylcinnamic aldehyde, CLARITONE®, Δ-damascone, dihydromyrcenol, E-, Z-isomers (3:1) of 3-methyl-2-octenoic acid ethyl esters, H&R odor neutralizer (D61012), phenylethyl alcohol, and Rosaphen®.

When the results of the panel were separated by gender, it was ascertained that none of the superior cross-adapting agents produced superior cross-adaptation in females. Certain of the superior cross-adapting agents from the combined panel produced adequate cross-adaptation at a level of p<0.05 in females. These included CLARITONE®, Δ-damascone, hexylcinnamic aldehyde, E, Z-isomers (3:1) of 3-methyl-2-octenoic acid ethyl esters, and H&R odor neutralizer (D61012). Vertocitral, which produced adequate cross-adaptation in the combined panel, also produced adequate cross-adaptation at the same level in the female panel members.

In male panel members, certain cross-adapting agents were identified among the adapting agents, where adequate cross-adaptation at a level of p<0.05 was produced. These cross-adapting agents included argumex, CEDRAMBER®, citronellol 950, citrylal, CLARITONE®, Δ-damascone, dihydromyrcenol, eugenol, floropal, menthyl acetate rf, H&R odor neutralizer (D61012), oryclone special, phenylethyl alcohol, Rosaphen®, Isobornyl Cyclohexanol, Sandranol®, tertahydro linalool, tonalide, and Z-isomer 3-methyl-2-pentenoic acid ethyl ester. Certain of the superior cross-adapting agents from the combined panel were also superior in males, producing superior cross-adaptation at a level of p<0.01. These included Δ-damascone, dihydromyrcenol, H&R odor neutralizer (D61012), and Rosaphen®. Eugenol, which was not among the aforementioned superior cross-adapting agents from the combined panel, appeared to be quite effective in males only, producing superior cross-adaptation at a level of p<0.01.

TABLE 1

Reduction of Intensity of Male Stress-Derived Odor

|  | p value Combined Panel | p value Male Panel | p value Female Panel |
|---|---|---|---|
| Agrumex | — | <0.05 | — |
| C14 Aldehyde | <0.05 | — | — |
| Ambrettolide | — | — | — |
| l-Carvone | <0.05 | — | — |
| CEDRAMBER ® | — | <0.05 | — |
| Citronellol 950 | <0.05 | <0.05 | — |
| Citrylal | <0.05 | <0.05 | — |
| CLARITONE ® | <0.01 | <0.05 | <0.05 |
| cpd Supra | — | — | — |
| α-Damascone | — | — | — |
| Δ-Damascone | <0.01 | <0.01 | <0.05 |
| Datilat | — | — | — |
| Dihydromyrcenol | <0.01 | <0.01 | — |
| Dynascone 10 | <0.05 | — | — |
| Eugenol | <0.05 | <0.01 | — |
| FARENAL ® | — | — | — |
| Floropal | <0.05 | <0.05 | — |
| GLOBALIDE ® | — | — | — |
| HEDIONE ® | — | — | — |
| Cis-3-Hexenol | — | — | — |
| E-isomer 3-methyl-2-pentenoic acid ethyl ester | <0.05 | — | — |
| Z-isomer 3-methyl-2-pentenoic acid ethyl ester | — | <0.05 | — |
| Hexyl Salicylate | — | — | — |

TABLE 1-continued

Reduction of Intensity of Male Stress-Derived Odor

|  | p value Combined Panel | p value Male Panel | p value Female Panel |
|---|---|---|---|
| Hexylcinnamic Aldehyde | <0.01 | — | <0.05 |
| ISO E SUPER ® | — | — | — |
| Isoananat | — | — | — |
| Menthyl Acetate rf | — | <0.05 | — |
| Mugetanol | — | — | — |
| Nerolione | — | — | — |
| E, Z-isomers (3:1) of 3-methyl-2-octenoic acid ethyl esters | <0.01 | — | <0.05 |
| H&R odor neutralizer ® (D61012) | <0.01 | <0.01 | <0.05 |
| Oryclone Special | <0.05 | <0.05 | — |
| Phenylethyl Alcohol | <0.01 | <0.05 | — |
| Rosaphen ® | <0.01 | <0.01 | — |
| Rose Oxide hc | <0.05 | — | — |
| Isobornyl Cyclohexanol | — | <0.05 | — |
| Sandranol ® | <0.05 | <0.05 | — |
| Tertahydro Linalool | — | <0.05 | — |
| Timbranol | — | — | — |
| Tonalide | — | <0.05 | — |
| Vertocitral | <0.05 | — | <0.05 | p < 0.01 Superior Cross-Adaptation
p < 0.05 Adequate Cross-Adaptation
— = Ineffective Cross-Adaptation Example 2

Deodorant Compositions for Men

Data from the cross-adaptation study was compiled and evaluated based on the effect each test material had on the magnitude of the stress-derived axillary odor intensity. Agents that produced the highest reduction in the stress-derived axillary odor intensity were labeled as "best" in Table 2. Agents that showed a moderate reduction were labeled as "good" and agent that had the least effect on reducing the magnitude of the stress-derived axillary odor intensity were labeled as "poor." A product can be constructed in a way to include as many "best" or "good" materials as desired and provide consumer acceptable hedonics.

TABLE 2

Magnitude of Reduction of Intensity of Male Stress-Derived Odor (MSDO)

|  | MSDO Males | MSDO Females |
|---|---|---|
| Agrumex | good | poor |
| C14 Aldehyde | good | poor |
| Ambrettolide | poor | poor |
| Anisic Aldehyde | — | — |
| Calone 1951 | — | — |
| l-Carvone | best | best |
| CEDRAMBER ® | good | poor |
| Citronellol 950 | good | good |
| Citrylal | best | good |
| CLARITONE ® | best | best |
| cpd Supra | poor | poor |
| α-Damascone | poor | poor |
| Δ-Damascone | best | good |
| Datilat | poor | poor |
| Dihydromyrcenol | best | good |
| Dynascone 10 | best | poor |
| Ethyl Vanillin | — | — |
| Eugenol | best | poor |
| Evernyl | — | — |
| FARENAL ® | poor | poor |
| Floropal | good | poor |

TABLE 2-continued

Magnitude of Reduction of Intensity
of Male Stress-Derived Odor (MSDO)

| | MSDO Males | MSDO Females |
|---|---|---|
| GLOBALIDE ® | good | poor |
| GLOBANONE ® | — | — |
| HEDIONE ® | poor | poor |
| Cis-3-Hexenol | good | good |
| Hexyl Salicylate | poor | poor |
| Hexylcinnamic Aldehyde | good | good |
| α-ionone | — | — |
| β-ionone | — | — |
| ISO E SUPER ® | poor | poor |
| Isoananat | best | poor |
| Isoraldeine 70 | — | — |
| Lilial | — | — |
| Lyral | — | — |
| MAJANTOL ® | — | — |
| Menthyl Acetate rf | best | poor |
| Mugetanol | good | poor |
| Nerolione | good | poor |
| E-, Z-isomers (3:1) of 3-methyl-2-octenoic acid ethyl esters | best | best |
| H&R odor neutralizer ® (D61012) | best | best |
| Oryclone Special | good | poor |
| Patchouli Oil | — | — |
| Phenylethyl Alcohol | good | good |
| E-isomer of 3-methyl-2-pentenoic acid ethyl ester | good | good |
| E-isomer of 3-methyl-2-octenoic acid ethyl ester | — | — |
| Z-isomer of 3-methyl-2-pentenoic acid ethyl ester | best | poor |
| Rosaphen ® | best | poor |
| Rose Oxide hc | poor | good |
| Isobornyl Cyclohexanol | good | poor |
| Sandranol ® | good | poor |
| Tetrahydro Linalool | best | poor |
| Timbranol | poor | poor |
| Tonalide | good | poor |
| Vertrocitral | good | best |

Best = Superior Cross-Adaptation
Good = Adequate Cross-Adaptation
Poor = Ineffective Cross-Adaptation
— = not tested The following examples, 2.1, 2.2, and 2.3, shown in Table 3, illustrate specific embodiments of an exemplary deodorant composition for men. The control is a typical formulation for an underarm antiperspirant stick that contains 1% of a masculine fragrance. The antiperspirant alone with this fragrance is considered a control because it does not contain any gender-specific cross adapting agents other than what may be used in a typical fragrance formulation. The fragrance is considered masculine in that its character is appropriate for a masculine product.

TABLE 3

Deodorant Compositions for Men (values indicate % of total).

| | | Examples | | |
|---|---|---|---|---|
| Ingredient | Control | 2.1 | 2.2 | 2.3 |
| REACH AZP-08 SUF | 24.00 | 24.00 | 24.00 | 24.00 |
| Cyclomethicone (Pentamer) | 24.00 | 23.25 | 23.25 | 23.50 |
| Polydecene (Silkflo 364 NF) | 20.00 | 20.00 | 19.25 | 19.37 |
| Polyethylene | 3.00 | 3.00 | 3.00 | 3.00 |
| Hydrogenated Castor Oil | 2.00 | 2.00 | 2.00 | 2.00 |
| Promyristyl PM-3 | 7.00 | 7.00 | 7.00 | 7.00 |
| PEG-8 Distearate | 3.00 | 3.00 | 3.00 | 3.00 |
| Stearyl Alcohol | 15.00 | 15.00 | 15.00 | 15.00 |
| Cab-O-Sil M-5 | 1.00 | 1.00 | 1.00 | 1.00 |

TABLE 3-continued

Deodorant Compositions for Men (values indicate % of total).

| | | Examples | | |
|---|---|---|---|---|
| Ingredient | Control | 2.1 | 2.2 | 2.3 |
| H&R Fougere Fragrance AC11227 | 1.00 | 1.00 | 1.00 | 1.00 |
| H&R Men's Accord AC11422 | 0.00 | 0.75 | 0.00 | 0.38 |
| H&R Encapsulated Men's Accord AC11422 In-Cap ® 464835 | 0.00 | 0.00 | 1.50 | 0.75 |
| Total | 100.00 | 100.00 | 100.00 | 100.00 |

Ingredients found in Table 2 determined by males to cross-adapt well with male stress-derived odor comprise 50.1% of Men's Accord AC11422. The accord comprises the following ingredients, shown in the following Table 4:

TABLE 4

Ingredients from Table 2 Contained in Men's Accord AC11422

| DESCRIPTION | INGREDIENT PARTS |
|---|---|
| AGRUMEX | 17.39 |
| C14 ALDEHYDE | 43.48 |
| CEDRAMBER ® | 17.39 |
| CLARITONE ® | 13.04 |
| EUGENOL | 0.87 |
| Δ-DAMASCONE | 0.09 |
| DIHYDROMYRCENOL | 69.57 |
| DYNASCONE 10 | 1.74 |
| GLOBALIDE ® | 65.22 |
| CIS-3-HEXENOL | 0.87 |
| HEXYLCINNAMIC ALDEHYDE | 43.48 |
| ISOANANAT | 4.35 |
| MENTHYL ACETATE RF | 43.48 |
| ORYCLONE SPECIAL | 17.39 |
| PHENYLETHYL ALCOHOL | 8.70 |
| ROSAPHEN ® | 13.04 |
| SANDRANOL ®SANDRANOL ® | 30.44 |
| TETRAHYDRO LINALOOL | 34.79 |
| VERTOCITRAL | 1.74 |
| TOTAL GENDER-SPECIFIC INGREDIENTS PARTS | 427.05 |
| TOTAL FRAGRANCE INGREDIENT PARTS | 852.00 |
| % GENDER-SPECIFIC | 50.1% |

The Encapsulated Men's Accord AC 11422 In-Cap® 464835 (H&R) fragrance formulation is created by spray drying, but variations can be made by those skilled in the art. The encapsulation formulation is not limited to these percentages or materials and can be formulated from many other carrier materials to release the accord as needed. The encapsulation formulation used in Table 3 comprises: 50% HiCap® 100 (supplied by National Starch) and 50% Men's Accord AC11422.

Examples 2.1, 2.2, and 2.3 show that it is possible to add Men's Accord AC11422 as oil, in encapsulated form and as a combination of both to an underarm formulation with another fragrance AC 11227.

Example 3

Cross-Adaptation of Female Stress-Derived Axillary Odor

A separate panel of 24 subjects (12 males and 12 females) tested samples of female stress-derived axillary odor with potential cross-adapting agents, some of which were not included in Example 1 above. Some of the subjects assessing the effectiveness of cross-adaptation of male stress-derived axillary odor were also used in the experiment with female secretions. However, these two experiments were treated as independent events. All panel members were screened for adequate use of magnitude estimation and further trained in its use during two to three training sessions. Subjects were tested with samples of female stress-derived axillary odor, prepared as described above for male stress-derived axillary odor, and compared to each of the potential cross-adapting agents, as set forth in Example 1 above. No subject was tested with all potential cross-adapting agents.

An array of adapting agents was tested for cross-adaptability against female stress-derived axillary odor. The adapting agents were selected from the following: agrumex, C14 aldehyde, ambrettolide, anisic aldehyde, calone 1951, l-carvone, CEDRAIVIBER®, citronellol 950, CLARITONE®, cpd supra, α-damascone, dihydromyrcenol, dynascone 10, ethyl vanillin, eugenol, evernyl, FARENAL®, floropal, GLOBALIDE®, GLOBANONE®, HEDIONE®, E-isomer of 3-methyl-2-pentenoic acid ethyl ester, Z-isomer 3-methyl-2-pentenoic acid ethyl ester, cis-3-hexenol, hexyl salicylate, hexylcinnamic aldehyde, α-ionone, β-ionone, ISO E SUPER®, isoananat, isoraldeine 70, lilial, lyral, MAJANTOL®, menthyl acetate rf, E-isomer of 3-methyl-2-octenoic acid ethyl ester, E-, Z-isomers (3:1) of 3-methyl-2-octenoic acid ethyl esters, H&R odor neutralizer (D61012), oryclone special, patchouli oil, phenylethyl alcohol, Rosaphen®, rose oxide hc, Sandranol® Sandranol®, and vertocitral.

Example 3 includes 31 of the adapting agents tested in Example 1, and 14 new adapting agents.

Magnitude estimations provided by each test subject were normalized compared to each subject's rating of a targeted malodor, e.g. female stress-derived axillary odor. A subject's rating of the intensity of a targeted malodor was standardized to a scale of 100, and then subsequent ratings after exposure to cross-adapting agents were standardized accordingly. Such standardized data was then analyzed for statistical significance and is reflected in Table 5.

With reference to Table 5, some differences and similarities between the studies of the female stress-derived axillary odor and the male stress-derived axillary odor (Example 1) were observed for the combined panel. (Compare Tables 1 & 5) First, many more adapting agents significantly reduced the perceived intensity of female stress-derived axillary odor than were noted in Example 1. Of the adapting agents tested, when the results of the panel as a whole were considered, thirty (30) were superior, reducing the perceived intensity of female malodors at a cross-adaptation level of $p<0.01$. These included: argumex, C14 aldehyde, ambrettolide, anisic aldehyde, calone 1951, l-carvone, CEDRAMBER®, CLARITONE®, cpd supra, cis-3-hexenol, dihydromyrcenol, dynascone 10, ethyl vanillin, eugenol, floropal, GLOBALIDE®, GLOBANONE®, hexylcinnamic aldehyde, α-ionone, β-ionone, isoraldeine 70, lyral, menthyl acetate rf, E-, Z-isomers (3:1) of 3-methyl-2-octenoic acid ethyl esters, oryclone special, patchouli oil, Rosaphen®, rose oxide hc, Sandranol®, and vertocitral. This may result, in part, because new adapting agents added to the candidate list were effective.

The adapting agents from Example 1 that were repeated in Example 3 are: agrumex, C14 aldehyde, ambrettolide, l-carvone, CEDRAMBER®, citronellol 950, CLARITONE®, cpd supra, α-damascone, Z-isomer 3-methyl-2-pentenoic acid ethyl ester, cis-3-hexenol, dihydromyrcenol, dynascone 10, eugenol, FARENAL®, floropal, GLOBALIDE®, HEDIONE®, hexyl salicylate, hexylcinnamic aldehyde, isoananat, menthyl acetate rf, E-, Z-isomers (3:1) of 3-methyl-2-octenoic acid ethyl esters, H&R odor neutralizer (D61012), oryclone special, phenylethyl alcohol, Rosaphen®, rose oxide hc, Sandranol®, and vertocitral. Of the adapting agents that were repeated in Example 3, in the combined panel, six (6) adapting agents produced the same degree of effectiveness with the female stress-derived axillary odor that were shown with the male malodor. For example, certain cross-adapting agents were superior, including CLARITONE®, dihydromyrcenol, E-, Z-isomers (3:1) of 3-methyl-2-octenoic acid ethyl esters, and Rosaphen®, reducing the perceived intensity of both male and female stress-derived axillary odors at cross-adaptation levels of $p<0.01$. (Tables 1 and 5). Alpha-damascone was the only adapting agent that was not significantly effective against either male or female malodors for the combined panels.

Where differences existed, certain adapting agents were significantly effective at reducing the perception of female stress-derived axillary odor, but were less effective against male stress-derived axillary odor. In fact, certain cross-adapting agents, including agrumex, ambrettolide, CEDRAIVIBER®, cpd supra, GLOBALIDE®, cis-3-hexenol, and menthyl acetate rf, provided superior cross-adaptation at levels of $p<0.01$ (Compare Table 1 and Table 5) for the female stress-derived axillary odor whereas they were ineffective against male stress-derived axillary odor. Other adapting agents, including C14 aldehyde, l-carvone, CEDRAMBER®, dynascone 10, eugenol, floropal, oryclone special, rose oxide hc, Sandranol®, and vertocitral significantly reduced the perception of female stress-derived axillary odor, but were merely adequate against male stress-derived axillary odor.

Phenylethyl alcohol provided superior reduction in the perception of male stress-derived axillary odor at a cross-adaptation level of $p<0.01$, but was merely adequate against female stress-derived odor at a cross-adaptation level of $p<0.05$.

Again, gender differences in response to the malodor were observed; however, more candidate cross-adapting odorants reduced the intensity of the female stress-derived axillary odor in male panel members than in female panel members. For example, CEDRAMBER®, CLARITONE®, and H&R odor neutralizer (D61012) were superior, $p<0.01$, in reducing the perception of female stress-derived odor in female panel members; whereas cross-adapting agents including anisic aldehyde, CEDRAIVIBER®, CLARITONE®, cis-3-hexenol, dihydromyrcenol, dynascone 10, ethyl vanillin, eugenol, floropal, hexylcinnamic aldehyde, α-ionone, β-ionone, isoraldeine 70, oryclone special, patchouli oil, Rosaphen®, rose oxide hc, Sandranol®, and, vertocitral were superior, $p<0.01$, in reducing the perception of female stress-derived odor in male panel members.

In the male panel members, cross-adapting agents including C14 aldehyde, ambrettolide, calone 1951, l-carvone, citronellol 950, cpd supra, dynascone 10, FARENAL®, GLOBANONE®, ISO E SUPER®, isoananat, lilial, lyral, MAJANTOL®, menthyl acetate rf, phenylethyl alcohol, and rose oxide hc adequately reduced the perception of female stress-derived odor, at a cross-adaptation level of $p<0.05$. In the female panel members, cross-adapting agents, including agrumex, calone 1951, CEDRAIVIBER®, cis-3-hexenol, floropal, GLOBALIDE®, patchouli oil, rose oxide hc, and vertocitral adequately reduced the perception of female stress-derived odor at a cross-adaptation level of $p<0.05$.

CLARITONE® and E-, Z-isomers (3:1) of 3-methyl-2-octenoic acid ethyl esters were superior at cross-adapting female stress-derived odor in both males and females.

Examples of gender differences are found in the comparison of the female panel members response with the cross-adapting agents agrumex, GLOBALIDE®, and H&R odor neutralizer (D61012) with that of the male response. For the female panel members, these cross-adapting agents reduced the perception of female stress-derived odor at a cross-adaptation level of p<0.05, (Table 5), whereas for the male panel members, they were ineffective. On the other hand, Rosaphen®, Sandranol®, ambrettolide, cpd supra, eugenol, oryclone special, hexylcinnamic aldehyde, α-ionone, isoraldeine 70, β-ionone, ethyl vanillin, and anisic aldehyde were ineffective in female panelists but were superior in male panelists at cross-adapting female stress-derived odor.

The results demonstrate that certain adapting agents are superior to others in reducing or blocking odors of biological origin and can be selectively used in deodorant formulations to achieve a desired result, such as, for example, to reduce or block the strongest odors, for example, those axillary odors produced under stressful conditions.

TABLE 5

Reduction of Intensity of Female Stress-Derived Odor

|  | p value Combined Panel | p value Male Panel | p value Female Panel |
|---|---|---|---|
| Agrumex | <0.01 | — | <0.05 |
| C14 Aldehyde | <0.01 | <0.05 | — |
| Ambrettolide | <0.01 | <0.05 | — |
| Anisic Aldehyde | <0.01 | <0.01 | — |
| Calone 1951 | <0.01 | <0.05 | <0.05 |
| l-Carvone | <0.01 | <0.05 | — |
| CEDRAMBER® | <0.01 | <0.01 | <0.05 |
| Citronellol 950 | — | <0.05 | — |
| CLARITONE® | <0.01 | <0.01 | <0.01 |
| cpd Supra | <0.01 | <0.05 | — |
| α-Damascone | — | — | — |
| Dihydromyrcenol | <0.01 | <0.01 | — |
| Dynascone 10 | <0.01 | <0.05 | — |
| Ethyl Vanillin | <0.01 | <0.01 | — |
| Eugenol | <0.01 | <0.01 | — |
| Evernyl | — | — | — |
| FARENAL® | <0.05 | <0.05 | — |
| Floropal | <0.01 | <0.01 | <0.05 |
| GLOBALIDE® | <0.01 | — | <0.05 |
| GLOBANONE® | <0.01 | <0.05 | — |
| HEDIONE® | <0.05 | — | — |
| E-isomer of 3-methyl-2-pentenoic acid ethyl ester | — | — | — |
| Z-isomer of 3-methyl-2-pentenoic acid ethyl ester | <0.05 | — | — |
| Cis-3-Hexenol | <0.01 | <0.01 | <0.05 |
| Hexyl Salicylate | <0.05 | — | — |
| Hexylcinnamic Aldehyde | <0.01 | <0.01 | — |
| α-ionone | <0.01 | <0.01 | — |
| β-ionone | <0.01 | <0.01 | — |
| ISO E SUPER® | <0.05 | <0.05 | — |
| Isoananat | <0.05 | <0.05 | — |
| Isoraldeine 70 | <0.01 | <0.01 | — |
| Lilial | — | <0.05 | — |
| Lyral | <0.01 | <0.05 | — |
| MAJANTOL® | <0.05 | <0.05 | — |
| Menthyl Acetate rf | <0.01 | <0.05 | — |
| E-isomer of 3-methyl-2-octenoic acid ethyl ester | <0.05 | — | — |
| E-, Z-isomers (3:1) of 3-methyl-2-octenoic acid ethyl esters | <0.01 | <0.01 | <0.01 |
| H&R odor neutralizer (D61012) | <0.05 | — | <0.05 |
| Oryclone Special | <0.01 | <0.01 | — |
| Patchouli Oil | <0.01 | <0.01 | <0.05 |
| Phenylethyl Alcohol | <0.05 | <0.05 | — |
| Rosaphen® | <0.01 | <0.01 | — |
| Rose Oxide hc | <0.01 | <0.05 | <0.05 |
| Sandranol® | <0.01 | <0.01 | — |
| Vertocitral | <0.01 | <0.01 | <0.05 | p < 0.01 Superior Cross-Adaptation
p < 0.05 Adequate Cross-Adaptation
— = Ineffective Cross-Adaptation Example 4

Deodorant Compositions for Women

Data from the cross-adaptation study was compiled and evaluated based on the effect each test material had on the magnitude of the stress-derived axillary odor intensity. Agents that produced the highest reduction in the stress-derived axillary odor intensity were labeled as "best" in Table 6. Agents that showed a moderate reduction were labeled as "good" and agent that had the least effect on reducing the magnitude of the stress-derived axillary odor intensity were labeled as "poor." A product can be constructed in a way to include as many "best" or "good" materials as desired and provide consumer acceptable hedonics.

TABLE 6

Magnitude of Reduction of Intensity of Female Stress-Derived Odor (FSDO)

|  | FSDO Males | FSDO Females |
|---|---|---|
| Agrumex | poor | best |
| C14 Aldehyde | good | good |
| Ambrettolide | poor | good |
| Anisic Aldehyde | best | good |
| Calone 1951 | good | good |
| l-Carvone | good | best |
| CEDRAMBER® | good | good |
| Citronellol 950 | good | good |
| Citrylal | — | — |
| CLARITONE® | best | good |
| cpd Supra | good | good |
| α-Damascone | poor | good |
| Δ-Damascone | — | — |
| Datilat | — | — |
| Dihydromyrcenol | best | good |
| Dynascone 10 | good | good |
| Ethyl Vanillin | best | poor |
| Eugenol | good | good |
| Evernyl | poor | good |
| FARENAL® | good | poor |
| Floropal | best | best |
| GLOBALIDE® | poor | good |
| GLOBANONE® | good | poor |
| HEDIONE® | poor | poor |
| Cis-3-Hexenol | best | good |
| Hexyl Salicylate | poor | good |
| Hexylcinnamic Aldehyde | good | poor |
| α-ionone | good | good |
| β-ionone | good | poor |
| ISO E SUPER® | poor | poor |
| Isoananat | good | poor |
| Isoraldeine 70 | best | poor |
| Lilial | good | poor |
| Lyral | good | poor |
| MAJANTOL® | good | poor |
| Menthyl Acetate rf | good | good |
| Mugetanol | — | — |
| Nerolioine | — | — |
| E-, Z-isomers (3:1) of 3-methyl-2-octenoic acid ethyl esters | best | best |
| H&R odor neutralizer (D61012) | poor | good |
| Oryclone Special | best | poor |
| Patchouli Oil | best | best |
| Phenylethyl Alcohol | good | poor |
| E-isomer of 3-methyl-2-pentenoic acid ethyl ester | poor | poor |
| E-isomer of 3-methyl-2-octenoic acid ethyl ester | good | poor |
| Z-isomer of 3-methyl-2-pentenoic acid ethyl ester | poor | poor |
| Rosaphen® | good | poor |
| Rose Oxide hc | good | good |
| Isobornyl Cyclohexanol | — | — |
| Sandranol® | good | good |

TABLE 6-continued

Magnitude of Reduction of Intensity
of Female Stress-Derived Odor (FSDO)

|  | FSDO Males | FSDO Females |
|---|---|---|
| Tetrahydro Linalool | — | — |
| Timbranol | — | — |
| Tonalide | — | — |
| Vetrocitral | best | best |

Best = Superior Cross-Adaptation
Good = Adequate Cross-Adaptation
Poor = Ineffective Cross-Adaptation
— = not tested The following Examples 4.1, 4.2, and 4.3 shown in Table 7 illustrate specific embodiments of an exemplary deodorant composition for women. The control is a typical formulation for an underarm antiperspirant stick that contains 1% of a feminine fragrance. The antiperspirant alone with this fragrance is considered a control because it does not contain any gender-specific cross adapting agents other than what may be used in a typical fragrance formulation. The fragrance is considered feminine in that its character is appropriate for a feminine product.

TABLE 7

Deodorant Compositions for Women (values indicate % of total).

|  |  | Examples | | |
|---|---|---|---|---|
| Ingredient | Control | 4.1 | 4.2 | 4.3 |
| REACH AZP-08 SUF | 24.00 | 24.00 | 24.00 | 24.00 |
| Cyclomethicone (Pentamer) | 24.00 | 23.25 | 23.25 | 23.50 |
| Polydecene (Silkflo 364 NF) | 20.00 | 20.00 | 19.25 | 19.37 |
| Polyethylene | 3.00 | 3.00 | 3.00 | 3.00 |
| Hydrogenated Castor Oil | 2.00 | 2.00 | 2.00 | 2.00 |
| Promyristyl PM-3 | 7.00 | 7.00 | 7.00 | 7.00 |
| PEG-8 Distearate | 3.00 | 3.00 | 3.00 | 3.00 |
| Stearyl Alcohol | 15.00 | 15.00 | 15.00 | 15.00 |
| Cab-O-Sil M-5 | 1.00 | 1.00 | 1.00 | 1.00 |
| H&R Citrus Powder Fragrance AC11414 | 1.00 | 1.00 | 1.00 | 1.00 |
| H&R Women's Accord AC11629 | 0.00 | 0.75 | 0.00 | 0.38 |
| H&R Encapsulated Women's Accord AC11629 In-Cap ® 469147 | 0.00 | 0.00 | 1.50 | 0.75 |
| Total | 100.00 | 100.00 | 100.00 | 100.00 |

Ingredients found in Table 6 determined by females to cross-adapt well with female stress-derived odor comprise 47.3% of Women's Accord AC11629. The accord comprises the following ingredients, shown in the following Table 8:

TABLE 8

Ingredients from Table 6 Contained in Women's Accord AC11629

| DESCRIPTION | INGREDIENT PARTS |
|---|---|
| AGRUMEX | 8.33 |
| C14 ALDEHYDE | 75.00 |
| AMBRETTOLIDE | 2.50 |
| ANISIC ALDEHYDE | 4.16 |
| CLARITONE ® | 12.50 |
| DIHYDROMYRCENOL | 75.00 |
| DYNASCONE 10 | 0.83 |
| EVERNYL | 3.33 |
| GLOBALIDE ® | 58.33 |
| HEXYL SALICYLATE | 41.66 |
| α-IONONE | 25.00 |
| CPD SUPRA | 8.33 |
| MENTHYL ACETATE RF | 62.50 |
| PATCHOULI OIL | 4.16 |
| SANDRANOL ® | 29.16 |
| VERTOCITRAL | 1.66 |
| TOTAL GENDER-SPECIFIC INGREDIENTS PARTS | 412.50 |
| TOTAL FRAGRANCE INGREDIENT PARTS | 872.67 |
| % GENDER-SPECIFIC | 47.3% |

The Encapsulated Women's Accord AC 11629 In-Cap® 469147 (H&R) fragrance formulation is created by spray drying, but variations can be made by those skilled in the art. The encapsulation formulation is not limited to these percentages or materials and can be formulated from many other carrier materials to release the accord as needed. The encapsulation formulation used in Table 7 comprises: 50% HiCap® 100 (supplied by National Starch) and 50% Women's Accord AC11629.

Examples 4.1, 4.2, and 4.3 show that it is possible to add Women's Accord AC11629 as oil, in encapsulated form and as a combination of both to an underarm formulation with another fragrance AC11414.

The examples provided herein are meant to illustrate the invention, not limit it. Those skilled in the art will recognize modifications, which are within the spirit and scope of the invention.

What is claimed:

1. A deodorant composition comprising a mixture of agents that block and/or reduce the perception of malodors, wherein said mixture consists of:
   agrumex (2-tert-butylcyclohexyl acetate);
   γ-undecalactone;
   cedryl methyl ether;
   2,4,4,7-tetramethyl-oct-6-en-3-one;
   eugenol (2-methoxy-1-hydroxy-4-allylbenzene);
   Δ-damascone (1-(2,6,6-trimethyl-3-cyclohexen-1-yl)-2-buten-1-one);
   dihydromyrcenol (2,6-dimethyl-7-octen-2-ol);
   dynascone 10 (1-(5,5-dimethyl-1-cyclohexen-1-yl)-4-penten-1-one);
   oxacyclohexadecen-2-one;
   cis-3-hexenol (cis-3-hexen-1-ol);
   hexylcinnamic aldehyde (alpha-hexylcinnamaldehyde);
   isoananat (acetic acid, (cyclohexyloxy)-, 2-propenyl-ester);
   menthyl acetate rf (4-menth-3-yl acetate);
   oryclone special (4-tertbutylcyclohexyl acetate);
   phenylethyl alcohol (2-phenylethyl alcohol);
   2-methyl-5-phenylpentan-1-ol;
   2-ethyl-4-(2,2,3-trimethyl-3-cyclopenten-1-yl)-2-buten-1-ol;
   tetrahydro linalool (3,7-dimethyloctan-3-ol); and
   vertocitral (2,4-dimethyl-3-cyclohexene-1-carboxaldehyde).

2. A deodorant composition comprising a mixture of agents that block and/or reduce the perception of malodors, wherein said mixture consists of:
   agrumex (2-tert-butylcyclohexyl acetate);
   Δ-undecalactone;
   ambrettolide (oxacycloheptadec-10-en-2-one);

anisyl aldehyde (4-methoxybenzaldehyde);
2,4,4,7-tetramethyl-oct-6-en-3-one;
dihydromyrcenol (2,6-dimethyl-7-octen-2-ol);
dynascone 10 (1-(5,5-dimethyl-1-cyclohexen-1-yl)-4-penten-1-one);
evernyl (methyl 2,4-dihydroxy-3,6-dimethylbenzoate);
oxacyclohexadecen-2-one;
hexyl salicylate (hexyl-2-hydroxybenzoate);
α-ionone (4-(2,2,6-trimethyl-2-cyclohexen-1-yl)-3-buten-2-one);
CPD supra (oxacyclohexadecan-2-one);
menthyl acetate rf (4-menth-3-yl acetate);
patchouli oil;
2-ethyl-4-(2,2,3-trimethyl-3-cyclopenten-1-yl)-2-buten-1-ol; and
vertocitral (2,4-dimethyl-3-cyclohexene-1-carboxaldehyde).

* * * * *